United States Patent [19]

Cebalo

[11] 3,959,303

[45] May 25, 1976

[54] 5-CYANOALKYL-1,3,4-THIADIAZOL-2-YLUREAS

[75] Inventor: Tony Cebalo, Indianapolis, Ind.

[73] Assignee: Eli Lilly and Company, Indianapolis, Ind.

[22] Filed: Oct. 15, 1974

[21] Appl. No.: 514,671

[52] U.S. Cl.............................. 260/306.8 D; 71/90; 424/270
[51] Int. Cl.².......................................... C07D 285/12
[58] Field of Search............................ 260/306.8 D Primary Examiner—Richard J. Gallagher
Attorney, Agent, or Firm—Joseph A. Jones; Everet F. Smith

[57] ABSTRACT

A group of new 1,3,4-thiadiazol-2-ylureas are characterized by a cyanoalkyl group at the 5-position. The alkyl group to which the cyano group is attached is always branched, and is preferably branched at the carbon atom adjacent to the ring. The compounds are also characterized by small alkyl or alkoxy groups on the urea nitrogens. The new compounds are outstandingly effective herbicides and are also effective, when used at low application rates, in the control of plant pathogens.

7 Claims, No Drawings

5-CYANOALKYL-1,3,4-THIADIAZOL-2-YLUREAS

BACKGROUND OF THE INVENTION

This invention belongs to the field of agricultural chemistry and relates to herbicides and plant fungicides. Herbicides and fungicides have become the basis of an enormous industry, and are commonly used in the culture of virtually every crop and ornamental plant. It has been abundantly proved that the proper use of herbicides, for the elimination of weeds which consume water and nutrients and shade the crop from the sun, and fungicides for the control of plant pathogens, is necessary to maximize production. Such agricultural chemicals, properly used, produce benefits, both in yield and in economic profit, which far outweigh the expense of the chemicals.

The 1,3,4-thiadiazol-2-ylureas have been the subject of research in agricultural chemistry. Some compounds of the group have been found to be herbicidal. For example, Driscoll, German Offenlegungsschrift No. 2,017,842, disclosed thiadiazolylureas having a vast assortment of 5-substituents including cyanoalkylthio substituents. Metzger, Belgian Pat. No. 721,034, showed such compounds having alkyl, alkenyl, cycloalkyl and alkylthio 5-substituents. Hoegerle, Belgian Pat. No. 725,984, disclosed thiadiazolylureas having perfluoroalkyl 5-substituents and a variety of substituents on the urea nitrogens, including cyanoalkyl substituents.

References which discuss the herbicidal activity of the 1,3,4-thiadiazolylureas include Cebalo, South African Pat. No. 69/1559, concerning such compounds having a 5-acyclic hydrocarbon group, and Cebalo, U.S. Pat. No. 3,726,892, concerning 5-sulfamoyl compounds.

SUMMARY OF THE INVENTION

The present invention provides to the agricultural chemical art new compounds of the formula

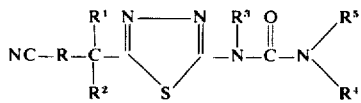

wherein
R represents a carbon-carbon bond or

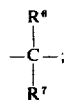

$R^1$, $R^2$, $R^6$ and $R^7$ independently represent hydrogen or $C_1$–$C_2$ alkyl,
provided that at least one of $R^1$, $R^2$, $R^6$ and $R^7$ must represent $C_1$–$C_2$ alkyl;
$R^3$ and $R^4$ independently represent $C_1$–$C_3$ alkyl;
$R^5$ represents hydrogen, $C_1$–$C_3$ alkyl or $C_1$–$C_3$ alkoxy.

A preferred group of compounds of this invention comprise those compounds of the above formula wherein $R^1$ and $R^2$ independently represent $C_1$–$C_2$ alkyl, and both $R^3$ and $R^4$ represent methyl.

The invention includes novel methods of using the compounds for the selective control of herbaceous weeds.

DESCRIPTION OF THE PREFERRED EMBODIMENT

In the above generic formula, the general chemical terms carry their normal meanings. The terms $C_1$–$C_2$ alkyl and $C_1$–$C_3$ alkyl refer to groups such as methyl, ethyl, propyl and isopropyl. The term $C_1$–$C_3$ alkoxy refers to groups such as methoxy, ethoxy, propoxy and isopropoxy.

The compounds below are typical of the invention. It will be understood that the named compounds do not delineate the scope of the invention, but are named merely to help those of chemical skill to understand the invention.

1-[5-(1-cyanoethyl)-1,3,4-thiadiazol-2-yl]-1,3-dimethylurea
1-[5-(1-cyanopropyl)-1,3,4-thiadiazol-2-yl]-1,3,3-trimethylurea
1-[5-(1-cyano-1-methylethyl)-1,3,4-thiadiazol-2-yl]-1-ethyl-3,3-dimethylurea
1-[5-(1-cyano-1-methylpropyl)-1,3,4-thiadiazol-2-yl]-3-ethyl-1-propylurea
1-[5-(2-cyano-1-methylethyl)-1,3,4-thiadiazol-2-yl]-3-ethyl-1-isopropyl-3-methylurea
1-[5-(1-cyanomethylpropyl)-1,3,4-thiadiazol-2-yl]-1-methyl-3-propylurea
1-[5-(2-cyano-2-methylethyl)-1,3,4-thiadiazol-2-yl]-1,3-dimethyl-3-propylurea
1-[5-(2-cyanobutyl)-1,3,4-thiadiazol-2-yl]-1-ethyl-3-isopropyl-3-methylurea
1-[5-(1-cyanomethyl-1-methylethyl)-1,3,4-thiadiazol-2-yl]-3-isopropyl-1,3-dimethylurea
1-[5-(1-cyanomethyl-1-methylpropyl)-1,3,4-thiadiazol-2-yl]-3-methoxy-1,3-dimethylurea
1-[5-(2-cyano-1-methylbutyl)-1,3,4-thiadiazol-2-yl]-3-ethoxy-1,3-diethylurea
1-[5-(2-cyano-2-methylpropyl)-1,3,4-thiadiazol-2-yl]-3-ethoxy-3-methyl-1-propylurea
1-[5-(2-cyano-1-ethylbutyl)-1,3,4-thiadiazol-2-yl]-1,3-dimethyl-3-propoxyurea
1-[5-(2-cyano-2-ethylbutyl)-1,3,4-thiadiazol-2-yl]-1,3-diethyl-3-isopropoxyurea
1-[5-(2-cyano-1-ethylpropyl)-1,3,4-thiadiazol-2-yl]-1,3,3-trimethylurea
1-[5-(1-cyanomethyl-1-ethylpropyl)-1,3,4-thiadiazol-2yl]-1-ethyl-3-propylurea
1-[5-(2-cyano-1,1-dimethylethyl)-1,3,4-thiadiazol-2yl]-1-isopropyl-3-methylurea
1-[5-(2-cyano-1,2-dimethylpropyl)-1,3,4-thiadiazol-2-yl]-3-ethoxy-1,3-dimethylurea
1-[5-(2-cyano-1-ethyl-2-methylpropyl)-1,3,4-thiadiazol-2-yl]-3-ethoxy-1-ethyl-3-propylurea
1-[5-(2-cyano-1-ethyl-2-methylbutyl)-1,3,4-thiadiazol-2-yl]-1,3,3-triethylurea
1-[5-(2-cyano-1,1-dimethylbutyl)-1,3,4-thiadiazol-2yl]-3-ethyl-1-methylurea
1-[5-(2-cyano-1,1-diethylpropyl)-1,3,4-thiadiazol-2-yl]-1,3-dipropylurea
1-[5-(2-cyano-2-ethyl-1-methylbutyl)-1,3,4-thiadiazol-2-yl]-1,3,3-trimethylurea
1-[5-(2-cyano-1,1-diethylbutyl)-1,3,4-thiadiazol-2-yl]-1,3-dimethyl-3-propylurea
1-[5-(2-cyano-1,2-diethylbutyl)-1,3,4-thiadiazole-2-yl]-1-ethyl-3-ethoxy-3-propylurea
1-[5-(2-cyano-1,1,2-trimethylpropyl)-1,3,4-thiadiazol-2-yl]-1,3-diethylurea
1-[5-(2-cyano-1-ethyl-1,2-dimethylpropyl)-1,3,4-thiadiazol-2-yl]-3-isopropyl-1,3-dimethylurea 1-[5-(2-cyano-1,1,2-trimethylbutyl)-1,3,4-thiadiazol-2-yl]-3-methoxy-1,3-dimethylurea
1-[5-(2-cyano-1,1-diethyl-2-methylpropyl)-1,3,4-thiadiazol-2-yl]-3 -ethyl-1,3-dimethylurea
1-[5-(2-cyano-1-ethyl-1,2-dimethylbutyl)-1,3,4-thiadiazol-2-yl]-1-ethyl-3-methoxy-3-methylurea
1-[5-(2-cyano-2-ethyl-1,1-dimethylbutyl)-1,3,4-thiadiazol-2-yl]-1,3-dimethyl-3-propoxyurea
1-[5-(2-cyano-1,2-diethyl-1-methylbutyl)-1,3,4-thiadiazol-2-yl]-1-ethyl-3-isopropoxy-3-methylurea
1-[5-(2-cyano-1,1-diethyl-2-methylbutyl)-1,3,4-thiadiazol-2yl]-1,3-dimethylurea
1-[5-(2-cyano-1,1,2-triethylbutyl)-1,3,4-thiadiazol-2yl]-1,3,3-trimethylurea The following are the preferred compounds of this invention.

1-[5-(1-cyano-1-methylethyl)-1,3,4-thiadiazol-2-yl]-1,3-dimethylurea
1-[5-(2-cyano-2-methylpropyl)-1,3,4-thiadiazol-2-yl]-1,3-dimethylurea
1-[5-(2-cyano-1,1-dimethylethyl)-1,3,4-thiadiazol-2-yl]-1,3-dimethylurea
1-(1-cyano-1-methylethyl)-1,3,4-thiadiazol-2-yl]-1,3,3-trimethylurea
1-[5-(2-cyano-1,1-dimethylethyl)-1,3,4-thiadiazol-2-yl]-1,3,3-trimethylurea The compounds of this invention are made by a synthesis which follows the known preparations of thiadiazolylureas. Compounds wherein R represents methylene are made in three steps. In the first step, a 4-alkylthiosemicarbazide is reacted above room temperature with a chlorine-substituted branched carboxylic acid in the presence of a reagent such as phosphorus oxychloride to form a 2-alkylamino-5-chloroalkyl-1,3,4-thiadiazole. Cf. U.S. Pat. No. 2,497,825, C.A. 44, 5919 (1950). In the second step, the thiadiazole is reacted with NaCN to form the second intermediate, a 2-alkylamino-5-cyanoalkyl-1,3,4-thiadiazole. Finally, the urea moiety of the molecule is formed by reaction with an alkylisocyanate, if $R^5$ in the desired product represents hydrogen, or with an appropriately substitued carbamoyl chloride to form a product wherein $R^5$ represents alkyl or alkoxy.

Compounds wherein R represents a carbon-carbon bond, so that the carbon atom to which the cyano group is attached is adjacent to the ring, can be made in only two steps. In the first step, a 4-alkylthiosemicarbazide is reacted with an α-cyanocarboxylic acid to form the intermediate 2-alkylamino-5-cyanoalkyl-1,3,4-thiadiazole. The urea moiety is then formed as described above.

All of the starting compounds used in the reactions are readily obtained, as an organic chemist will observe.

The following preparative examples are included to assist those skilled in organic chemistry in the preparation of the compounds of this invention. The first example shows the formation of the thiadiazole ring.

EXAMPLE 1

5-(2-chloro-1,1-dimethylethyl)-2-methylamino-1,3,4-thiadiazole

An 87.2 g. portion of 4-methylthiosemicarbazide and 113.2 g. of 3-chloro-2,2-dimethylpropionic acid were suspended in 300 ml. of dioxane. The mixture was heated to 90°C. and 139.5 g. of phosphorus oxychloride was added dropwise while holding the temperature constant. After the addition was complete, the reaction mixture was stirred at 90°C. for three hours. The mixture was then allowed to cool and stand overnight at room temperature.

In the morning, the reaction was reheated and stirred at 100°C. for 1 hour more. Then, the mixture was cooled, and the dioxane was decanted off. The remaining solids were dissolved in warm water and the pH was adjusted to 8 with $NH_4OH$. The solids were filtered out of the aqueous mixture and washed with water on the filter. The solids were extracted were extracted with ethyl acetate, and the organic solution was washed with water and dried over anhydrous $Na_2SO_4$. The solvent was evaporated under vacuum and the solids remaining after evaporation were 136.4 g. of 5-(2-chloro-1,1-dimethylethyl)-2-methylamino-1,3,4-thiadiazole, m.p. 85°–88°C.

The next example illustrates the formation of the cyanoalkyl group.

EXAMPLE 2

5-(2-cyano-1,1-dimethylethyl)-2-methylamino-1,3,4-thiadiazole

A 20.5 g. portion of the intermediate prepared in Example 1 and 10 g. of NaCN were added to 50 ml. of dimethylsulfoxide and heated at 110°C. for 2 hours. The reaction mixture was then cooled and poured into 300 ml. of water, which was then extracted with a total of 1 liter of ethyl ether. The combined ether extracts were dried over anhydrous $Na_2SO_4$, filtered, and evaporated to dryness yielding a dark oil. The oil was chromatographed on a silica gel column, eluting with ethyl acetate. The desired intermediate product, 5-(2-cyano-1,1-dimethylethyl)-2-methylamino-1,3,4-thiadiazole, m.p. 65°–67°C., was isolated in the amount of 750 mg.

The following examples are illustrative of the formation of the urea moieties of the compounds.

EXAMPLE 3

1-[5-(2-cyano-1,1-dimethylethyl)-1,3,4-thiadiazol-2-yl]-1,3-dimethylurea

A 1.2 g. portion of the intermediate product of Example 2 was added to 20 ml. of toluene and 600 mg. of methylisocyanate was added. The reaction mixture was heated at reflux temperature for 16 hours, after which it was cooled and concentrated to dryness yielding 850 mg. of solid 1-[5-(2-cyano-1,1-dimethylethyl)-1,3,4-thiadiazol-2-yl]-1,3-dimethylurea, m.p. 133°–135°C. The product was identified by infrared analysis, nuclear magnetic resonance analysis and elemental microanalysis, the results of which follow.

|   | Theoretical | Found |
|---|---|---|
| C | 47.41% | 47.24% |
| H | 5.97 | 6.04 |
| N | 27.65 | 27.44 |

EXAMPLE 4

1-[5-(1-cyano-1-methylethyl)-1,3,4-thiadiazol-2-yl]-1,3,3-trimethylurea

A 3 g. portion of 5-(1-cyano-1-methylethyl)-2-methylamino-1,3,4-thiadiazole, made from 4-methylthiosemicarbazide and 2-cyano-2-methylpropionic acid, was dissolved in 40 ml. of dimethylformamide and 2 g. of N,N-dimethylcarbamoyl chloride was added. The mixture was cooled to 0°–10°C. and 0.72 g. of sodium hydride was added over a 30-minute period. The reaction mixture was then allowed to warm to room temperature and was stirred overnight. In the morning, the mixture was poured over crushed ice and the aqueous mixture was extracted with ethyl acetate. The organic layer was washed with water, dried over anhydrous $Na_2SO_4$, and concentrated under vacuum to an oil. The product was purified by chromatography over a silica gel column with 30 percent hexane/70 percent petroleum ether as eluent. Evaporation of the product-containing fraction under vacuum yielded 600 mg. of 1-[5-(1-cyano-1-methylethyl)-1,3,4-thiadiazol-2-yl]-1,3,3-trimethylurea, m.p. 92°–94°C., which was identified by nuclear magnetic resonance analysis, and by elemental microanalysis with the following results.

|   | Theoretical | Found |
|---|---|---|
| C | 47.41% | 47.13% |
| H | 5.97 | 5.74 |
| N | 27.65 | 27.37 |

The synthetic methods described above are used, with such minor variations as any chemist can supply, to make all the compounds of the invention, such as the following.

EXAMPLE 5

1-[5-(1-cyano-1-methylethyl)-1,3,4-thiadiazol-2-yl]-1,3-dimethylurea, m.p. 152°–154°C.

EXAMPLE 6

1-[5-(2-cyano-2-methylpropyl)-1,3,4-thiadiazol-2yl]-1,3-dimethylurea, m.p. 162°–164°C.

EXAMPLE 7

1-[5-(2-cyano-1,1-dimethylethyl)-1,3,4-thiadiazol-2-yl]-1,3,3-trimethylurea, oil.

The herbicidal properties of the new compounds have been evaluated in controlled tests conducted as follows. Seeds of crop and weed plants were planted in a fertile, sandy soil in flat metal trays having provision for drainage. The various seeds were planted at depths appropriate for good emergence of the individual species.

The compound to be tested was formulated in an appropriate organic solvent, with emulsifiers, and was dispersed in water at a convenient concentration for application. The quantity of compound to be applied per unit area of soil was chosen for each test, the weight of compound per tray was calculated, and an amount of the aqueous dispersion supplying that quantity of compound was evenly applied over each tray.

When the preemergence efficacy of the compound was to be evaluated, the compound was applied to the surface of the soil the same day that the seeds were planted. The treated trays were then put in the greenhouse and allowed to grow under observation until untreated control plants had emerged and injury to the emerged treated plants, if any, was clearly evident when compared with controls. The treated trays were then rated for injury by a skilled observer.

When the postemergence activity of a compound was to be evaluated, the aqueous dispersion of the compound was applied to emerged plants about 12 days after planting. The treated plants were then put back into the greenhouse and observed along with untreated controls for about two weeks, after which the plants were rated on a 1–5 scale, wherein 5 indicates dead plants or no emergence, and 1 indicates normal plants.

Only exemplary results observed in the testing of the new compounds will be given here. Not all compounds were tested against each plant species. A dash in the tables indicates that the compound was not tested.

Table 1

| Compound of Example No. | Rate of Appln. kg./ha. | Corn | Cotten | Soybean | Wheat | Alfalfa | Sugar Beet | Rice | Cucumber | Tomato | Barnyardgrass |
|---|---|---|---|---|---|---|---|---|---|---|---|
| 3 | 1.1 | 1 | 1 | 1 | 1 | 1 | 2 | 1 | 3 | 2 | 1 |
|   | 4.5 | 1 | 1 | 2 | 1 | 1 | 4 | 2 | 3 | 2 | 2 |
|   | 9.0 | 1 | — | — | — | — | — | — | — | — | — |
| 4 | 0.56 | 1 | 1 | 1 | 1 | 1 | 2 | 1 | 3 | 1 | 3 |
|   | 4.5 | 1 | 2 | 2 | 1 | 3 | 3 | 1 | 2 | 2 | 3 |
| 5 | 0.56 | 1 | 1 | 1 | 1 | 1 | 1 | 1 | 1 | 1 | 3 |
|   | 1.1 | 1 | 1 | 1 | 1 | 2 | 2 | 2 | 2 | 2 | 2 |
| 6 | 9.0 | 1 | — | — | — | — | — | — | — | — | — |
| 7 | 1.1 | 1 | 1 | 1 | 1 | 2 | 3 | 1 | 1 | 1 | 1 |
|   | 9.0 | 2 | — | — | — | — | — | — | — | — | — |

| Compound of Example No. | Rate of Appln. kg./ha. | Lambsquarter | Large Crabgrass | Mustard | Pigweed | Foxtail | Wild Oat | Velvetleaf | Jimsonweed | Morning Glory | Zinnia |
|---|---|---|---|---|---|---|---|---|---|---|---|
| 3 | 1.1 | 3 | 2 | 1 | 2 | 2 | 1 | 3 | 1 | 1 | — |
|   | 4.5 | 4 | 3 | 2 | 4 | 3 | 3 | 4 | 3 | 3 | — |
|   | 9.0 | — | 3 | — | 4 | 3 | — | 5 | — | 3 | 5 |
| 4 | 0.56 | 2 | 1 | 2 | 2 | 2 | 2 | 2 | 2 | 1 | 1 |
|   | 4.5 | 4 | 4 | 3 | 4 | 3 | 3 | 5 | 2 | 2 | 3 |
| 5 | 0.56 | 3 | 2 | 1 | 3 | 2 | 1 | 3 | — | 1 | 1 |
|   | 1.1 | 3 | 4 | 3 | 3 | 3 | 2 | 4 | — | 2 | 2 |
| 6 | 9.0 | — | 1 | — | 2 | 1 | — | 3 | — | 1 | 1 |
| 7 | 1.1 | 3 | 2 | 2 | 3 | 2 | 3 | 2 | 2 | 1 | 1 |
|   | 9.0 | — | 3 | — | 4 | 3 | — | 4 | — | 2 | 4 |

Table 2

| Compound of Example No. | Rate of Appln. kg./ha. | Postemergence | | | | | | |
|---|---|---|---|---|---|---|---|---|
| | | Corn | Large Crab-grass | Pig-weed | Fox-tail | Vel-vet-leaf | Morn-ing Glory | Zinnia |
| 3 | 1.1 | 2 | 4 | 5 | 4 | 5 | 4 | 5 |
| | 4.5 | 5 | 5 | 5 | 5 | 5 | 5 | 5 |
| | 9.0 | 5 | 5 | 5 | 5 | 5 | 5 | — |
| 4 | 0.07 | 1 | 2 | 3 | 3 | 4 | 4 | — |
| | 0.56 | 3 | 4 | 5 | 4 | 5 | 5 | 5 |
| | 4.5 | 4 | 5 | 5 | 5 | 5 | 5 | 5 |
| 5 | 0.07 | 2 | 3 | 5 | 3 | 5 | 3 | 3 |
| | 0.56 | 2 | 3 | 4 | 4 | 5 | 4 | 4 |
| | 1.1 | 4 | 4 | 5 | 5 | 5 | 5 | 5 |
| 6 | 2.2 | 1 | 3 | 4 | 3 | 3 | 2 | 2 |
| | 9.0 | 1 | 2 | 4 | 2 | 4 | 3 | — |
| 7 | 0.56 | 2 | 3 | 4 | 3 | 4 | 3 | 4 |
| | 1.1 | 2 | 3 | 5 | 3 | 4 | 4 | 4 |
| | 9.0 | 5 | 5 | 5 | 5 | 5 | 5 | 5 |

The best use of the new compounds described here is in the herbicidal method of selectively killing herbaceous weeds which is an important embodiment of the present invention, and which comprises contacting the weeds with an herbicidally-effective amount of one of the new compounds. As has been demonstrated, the compounds and the method are herbicidally effective when the weeds are contacted either postemergence, by direct contact with the weed, or preemergence, by soil contact with the weed seedling or with the germinating seed, which is here regarded as a part of the weed.

The compounds effectively control many different species and types of plants. The method is thus effective, when proper effective rates are used, in the control of virtually any herbaceous plant which is a weed by virtue of growing where it is not wanted. As the exemplary data above show, the compounds are safe to a number of useful crops at rates which control many weeds, and can thus be used for the control of weeds growing in such crops. The compounds can also be used for complete control of weeds where bare earth is desired.

For example, the following weed plants are typical of those controlled.

aster, rough (*Aster radula*)
barnyardgrass (*Echinochloa crus-galli*)
bedstraw, catchweed (*Galium aparine*)
beggarweed, Florida (*Desmodium tortuosum*)
brome, ripgut (*Bromus rigidus*)
burdock, common (*Arctium minus*)
carpetweed (*Mollugo verticillata*)
carrot, wild (*Daucus carota*)
catsclaw (*Caesalpinia sepiaria*)
chickweed (*Stellaria media*)
cocklebur, common (*Xanthium pensylvanicum*)
crowfootgrass (*Dactyloctenium aegyptium*)
dandelion, common (*Taraxacum officinale*)
dock, curly (*Rumes crispus*)
fennel, dog (*Eupatorium capillifolium*)
fiddleneck, tarweed (*Amsinckia lycopsoides*)
fleabane, rough (*Erigeron strigosus*)
foxtail, green (*Setaria viridis*)
goldenrod, Canada (*Solidago canadensis*)
hemlock, poison (*Conium maculatum*)
horseweed (*Conyza canadensis*)
lettuce, prickly (*Lactuca serriola*)
mallow, common (*Malva neglecta*)
mullein, common (*Verbascum thapsus*)
orchardgrass (*Dactylis glomerata*)
panicum, Texas (*Panicum texanum*)
pigweed, redroot (*Amaranthus retroflexus*)
plantain, buckhorn (*Plantago lanceolata*)
ragweed, giant (*Ambrosia trifida*)
sage, prairie (*Artemisia ludoviciana* var. *gnaphalodes*)
saltgrass, desert (*Distichlis stricta*)
sida, prickly (*Sida spinosa*)
thistle, bull (*Cirsium vulgare*)
toadflax, yellow (*Linaria vulgaris*)
vetch, (*Vicia* spp.)
wildrye, giant (*Elymus condensate*)
willow, meadow (*Salix petiolaris*)
witchgrass (*Panicum capillare*)
yarrow, common (*Achillea millefolium*)

The usual range of application rates of the compounds is from about 0.05 to about 20 kg./ha. A preferred range is from about 1 to about 10 kg./ha. It will be understood that, due to unusual conditions of temperature, rainfall or soil organic matter, it will occasionally be necessary to use application rates either higher or lower than the range described here. In general, however, skilled plant scientists will find that the compounds are most effective and economical when used at a rate in the described range. Of course, some weed species require higher application rates than others, as the examples illustrate.

It is not implied that all weeds growing in the treated area will be killed whenever one of the new compounds is applied thereto. The percentage of the weed population which will be killed depends on the age and vigor of the weeds at the time of application, the application rate, and the characteristics of the particular compound chosen. Those weeds which are not killed by the application will be injured to a greater or lesser degree depending on the same factors. Since the injury of weeds allows the crop to outgrow and shade out the weeds, merely injuring weeds confers a substantial benefit to the crop.

The new compounds have also been found to be useful in the control of plant pathogens, when applied at rates lower than the most effective herbicidal rates. For example, application of 1-[5-(1-cyano-1-methylethyl)-1,3,4-thiadiazol-2-yl]-1,3,3-trimethylurea to young greenhouse-grown plants which were subsequently infected with pathogens produced excellent control of powdery mildew of bean and complete control of anthracnose disease of cucumber when applied to the foliage as an aqueous dispersion containing 400 ppm. by weight of the compound.

Further, the new compound 1-[5-(1-cyano-1-methylethyl)-1,3,4-thiadiazol-2-yl]-1,3-dimethylurea also gave complete control of powdery mildew when applied at 400 ppm. and excellent control of bean rust when applied at 100 ppm. concentration. The same compound, when tested against diseases of small grains, was found to produce excellent control of powdery mildew, leaf rust and leaf spot of wheat.

Some injury to the host plants resulted from the use of the compounds to control plant pathogens.

The new compounds are normally used for either weed control or plant pathogen control in the form of agricultural formulations, although it is, of course, possible to apply the compounds in the pure form. In general, the formulations are the same, whether the compound is to be used as an herbicide or as a fungicide.

Very often, the compounds are formulated as concentrated compositions which are applied either to the soil or the foliage in the form of water dispersions or emulsions containing in the range of from about 0.1 percent to a few percent of the compound. Water-dispersible or emulsifiable compositions are either solids usually known as wettable powders, or liquids usually known as emulsifiable concentrates. Wettable powders comprise an intimate, finely-divided mixture of the thiadiazolylurea, an inert carrier and surfactants. The concentration of the thiadiazolylurea is usually from about 10 percent to about 90 percent. The inert carrier is usually chosen from among the attapulgite clays, the montmorillonite clays, the diatomaceous earths or the purified silicates. Effective surfactants, comprising from about 0.5 percent to about 10 percent of the wettable powder, are found among the sulfonated lingnins, the condensed napthalenesulfonates, the naphthalenesulfonates, the alkylbenzenesulfonates, the alkyl sulfates and nonionic surfactants such as ethylene oxide adducts of phenol.

Typical emulsifiable concentrates of the new compounds comprise a convenient concentration of the thiadiazolylurea, such as from about 100 to about 500 g. per liter of liquid, dissolved in an inert carrier which is a mixture of water-immiscible solvent and emulsifiers. Useful organic solvents include the aromatics, especially the xylenes, and the petroleum fractions, especially the high-boiling naphthalenic and olefinic portions of petroleum. Many other organic solvents may also be used such as the terpenic solvents, and the complex alcohols such as 2-ethoxyethanol. Suitable emulsifiers for emulsifiable concentrates are chosen from the same types of surfactants used for wettable powders.

When a thiadiazolylurea is to be applied to the soil, as for a preemergence application of the compound, it is convenient to use a granular or pellet formulation. Such a formulation typically comprises the compound dispersed on a granular inert carrier such as coarsely ground clay. The particle size of granules usually ranges from about 0.1 to about 3 mm.; pellets range from about 3 to 12 mm. in size. The usual formulation process for granules comprises dissolving the compound in an inexpensive solvent and applying the solution to the carrier in an appropriate solids mixer. Somewhat less economically, the compound may be dispersed in a dough composed of damp clay or other inert carrier, which is then dried and coarsely ground to produce the desired granular product. Pellets are made by processing a powdered mix of carrier and compound in a pellet mill.

The usual agricultural chemical application equipment may be used for the application of formulations of the new compounds. Water-dispersed formulations are readily applied either to the soil or to foliage by means of sprayers which may be hand-carried, tractor-mounted, self-propelled, or towed. Granular formulations are applied by any of the many metering applicators which are in wide use. The operator of the application equipment need only take care to apply an amount of the formulation per unit area of land which supplies the desired application rate of the thiadiazolylurea, and to apply it evenly throughout the area to be treated.

I claim

1. A compound of the formula

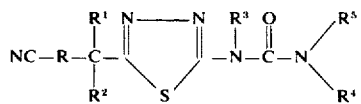

wherein

R represents a carbon-carbon bond or

$R^1$, $R^2$, $R^6$ and $R^7$ independently represent hydrogen or $C_1$–$C_2$ alkyl, provided that at least one of $R^1$, $R^2$, $R^6$ and $R^7$ must represent $C_1$–$C_2$ alkyl;

$R^3$ and $R^4$ independently represent $C_1$–$C_3$ alkyl;

$R^5$ represents hydrogen, $C_1$–$C_3$ alkyl or $C_1$–$C_3$ alkoxy.

2. A compound of claim 1 whrein $R^1$ and $R^2$ independently represent $C_1$–$C_2$ alkyl, and $R^3$ and $R^4$ represent methyl.

3. The compound of claim 2 which is 1-[5-(1-cyano-1-methylethyl)-1,3,4-thiadiazol-2-yl]-1,3-dimethylurea.

4. The compound of claim 2 which is 1-[5-(2-cyano-1,1-dimethylethyl)-1,3,4-thiadiazol-2-yl]-1,3-dimethylurea.

5. The compound of claim 2 which is 1-[5-(1-cyano-1-methylethyl)-1,3,4-thiadiazol-2-yl]-1,3,3-trimethylurea.

6. The compound of claim 2 which is 1-[5-(2-cyano-1,1-dimethylethyl)-1,3,4-thiadiazol-2-yl]-1,3,3-trimethylurea.

7. The compound of claim 1 which is 1-[5-(2-cyano-2-methylpropyl)-1,3,4-thiadiazol-2-yl]-1,3-dimethylurea.

* * * * *